United States Patent
Hamm et al.

(10) Patent No.: US 9,011,753 B2
(45) Date of Patent: Apr. 21, 2015

(54) METHOD FOR TREATING A PLASTIC PART, METHOD FOR MANUFACTURING A DRUG DELIVERY DEVICE AND DRUG DELIVERY DEVICE

(75) Inventors: German F. Hamm, Bad Soden-Salmünstr (DE); Steffen Raab, Frankfurt am Main (DE); Udo Stauder, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 284 days.

(21) Appl. No.: 13/498,907

(22) PCT Filed: Sep. 29, 2010

(86) PCT No.: PCT/EP2010/064431
§ 371 (c)(1),
(2), (4) Date: Aug. 3, 2012

(87) PCT Pub. No.: WO2011/039238
PCT Pub. Date: Apr. 7, 2011

(65) Prior Publication Data
US 2012/0302963 A1     Nov. 29, 2012

(30) Foreign Application Priority Data
Sep. 30, 2009  (EP) .................................... 09171770

(51) Int. Cl.
*B29C 59/16*     (2006.01)
*B29C 71/02*     (2006.01)
(Continued)

(52) U.S. Cl.
CPC ............ *B29C 71/02* (2013.01); *A61M 5/31525* (2013.01); *A61M 5/31533* (2013.01); *A61M 2005/3126* (2013.01);
(Continued)

(58) Field of Classification Search
CPC ........... B29C 2035/0822; B29C 71/02; B29C 35/0272; B29C 65/1629; B29C 59/16; B29C 59/007
USPC .......................................................... 264/446
See application file for complete search history.

(56) References Cited

U.S. PATENT DOCUMENTS

| 3,678,141 A * | 7/1972 | Metcalfe et al. ............... 264/494 |
| 2007/0184279 A1 | 8/2007 | Hartley et al. |
| 2009/0318861 A1* | 12/2009 | Corcoran et al. .......... 604/96.01 |

FOREIGN PATENT DOCUMENTS

| EP | 1852241 | 11/2007 |
| WO | 2007/054365 | 5/2007 |

OTHER PUBLICATIONS

International Preliminary Report on Patentability for International App. No. PCT/EP2010/064431, issued Apr. 3, 2012.
(Continued)

*Primary Examiner* — Kevin C Sirmons
*Assistant Examiner* — Deanna K Hall
(74) *Attorney, Agent, or Firm* — McDonnell Boehnen Hulbert & Berghoff LLP

(57) ABSTRACT

Method for treating a plastic part, which comprises a surface, comprising the steps: A) irradiating at least a part of the surface with a treatment radiation to obtain a modified surface area, the modified surface area being capable of absorbing a heating radiation to an extent greater than the unmodified surface area, and B) irradiating the modified surface area with the heating radiation at least in a section so that the plastic part is heated and softened in a region defined by the irradiated section of the modified surface area.

12 Claims, 4 Drawing Sheets

(51) Int. Cl.
    *B29C 35/02*     (2006.01)
    *B29C 65/00*     (2006.01)
    *B29C 71/04*     (2006.01)
    *A61M 5/315*     (2006.01)
    *A61M 5/31*     (2006.01)
    *B29C 65/16*     (2006.01)
    *B29C 35/08*     (2006.01)
    *B29K 27/18*     (2006.01)
    *B29K 67/00*     (2006.01)
    *B29K 105/00*     (2006.01)
    *B29L 31/00*     (2006.01)

(52) U.S. Cl.
CPC ... *A61M 2205/6063* (2013.01); *B29C 35/0266* (2013.01); *B29C 35/0272* (2013.01); *B29C 65/1616* (2013.01); *B29C 65/1629* (2013.01); *B29C 65/1696* (2013.01); *B29C 66/028* (2013.01); *B29C 66/1122* (2013.01); *B29C 66/1142* (2013.01); *B29C 66/43* (2013.01); *B29C 66/71* (2013.01); *B29C 71/04* (2013.01); *B29C 2035/0822* (2013.01); *B29C 2035/0827* (2013.01); *B29C 2035/0838* (2013.01); *B29K 2027/18* (2013.01); *B29K 2067/006* (2013.01); *B29K 2105/0032* (2013.01); *B29K 2105/005* (2013.01); *B29L 2031/753* (2013.01); *B29L 2031/7544* (2013.01); *B29C 65/1674* (2013.01)

(56) References Cited

OTHER PUBLICATIONS

European Search Report for European App. No. 09171770, completed Mar. 5, 2010.
International Search Report for International App. No. PCT/EP2010/064431, completed Jan. 13, 2011.

\* cited by examiner

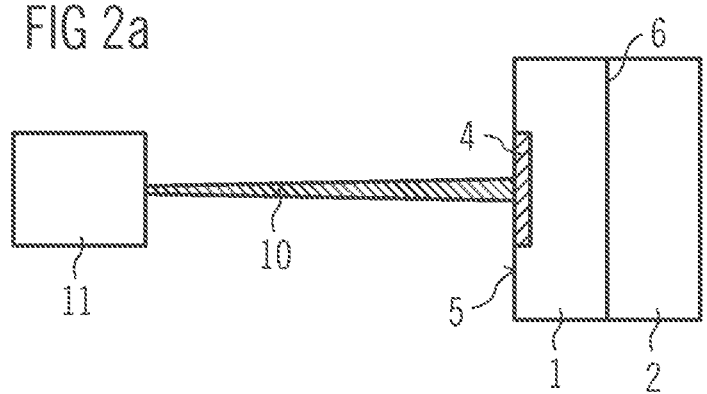
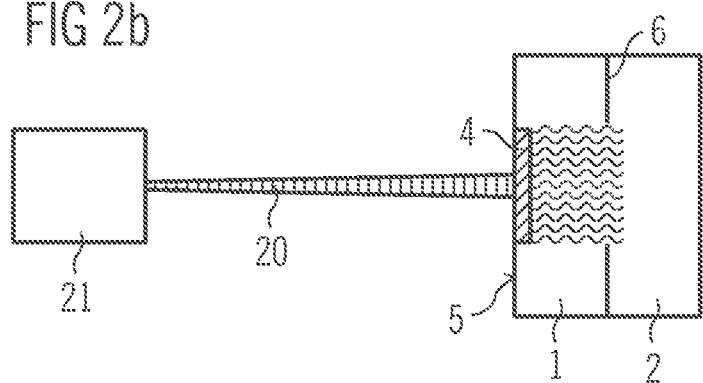
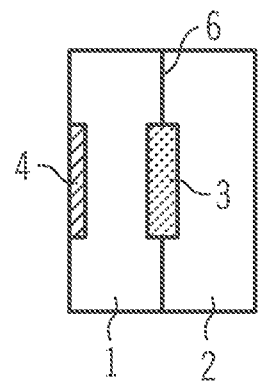

METHOD FOR TREATING A PLASTIC PART, METHOD FOR MANUFACTURING A DRUG DELIVERY DEVICE AND DRUG DELIVERY DEVICE

CROSS REFERENCE TO RELATED APPLICATIONS

The present application is a U.S. National Phase Application pursuant to 35 U.S.C. §371 of International Application No. PCT/EP2010/064431 filed Sep. 29, 2010, which claims priority to European Patent Application No. 09171770.2 filed on Sep. 30, 2009. The entire disclosure contents of these applications are herewith incorporated by reference into the present application.

FIELD OF INVENTION

The present disclosure relates to a method for treating a plastic part, which comprises a surface which may be reflective for a heating radiation. Furthermore, the disclosure relates to a method for manufacturing a drug delivery device according to this method and the drug delivery device itself.

BACKGROUND

One problem when treating a plastic part which has a surface which is considerable reflective for a radiation of a certain wavelength is that the surface of the plastic part, and, therefore, the plastic part itself cannot be easily processed with a method which requires absorption of this particular radiation.

SUMMARY

It is an object of the present disclosure to provide an improved or alternative method for treating a plastic part. Also an improved or alternative drug delivery device should be provided.

This object may be achieved, for example, by the subject matter of the independent claims. Further advantageous embodiments may be the subject matter of dependent claims.

According to one aspect the method for treating a plastic part, which comprises a surface, comprises the steps: A) irradiating at least a part of the surface with a treatment radiation to obtain a modified surface area, the modified surface area being capable of absorbing a heating radiation to an extent greater than the unmodified surface area, and B) irradiating the modified surface area with the heating radiation at least in a section so that the plastic part is heated and softened in a region defined by the irradiated section of the modified surface area.

By treating at least a part of the surface with the treatment radiation the surface may change its characteristics, e.g. its optical characteristics. The result of the treatment may be a modified surface area being capable of absorbing the heating radiation to an extent greater than the unmodified surface area. The unmodified surface area of the plastic part may now be more reflective for the heating radiation than the modified surface area. The modified surface area of the surface of the plastic part may have an increased absorption coefficient for the heating radiation as compared to the unmodified surface area of the surface of the plastic part.

By absorbing the energy of the heating radiation a region of the plastic part may be softened. In the context of this disclosure "softened" may mean that the plastic part is only softened but not capable of flowing in the region. But it may also mean that the plastic part absorbs so much energy that the plastic part is melted in that region. The melted region of the plastic part is expediently flowable. The region may, for example, be heated above its glass transition temperature.

In one aspect of the method at least a part of the surface of the plastic part which is not irradiated with the treatment radiation is unsoftenable or considerably less softenable by the heating radiation which softens the plastic part in the region defined by the irradiated section of the modified surface area. In particular, the heating radiation which may have been totally reflected or nearly totally reflected by the unmodified surface area is considerably absorbed by the modified surface area.

Accordingly, the modified surface area may define the region in which the plastic part is softenable by the heating radiation. Thus, by modifying the surface locally, one or more localized softenable regions of the plastic part may be defined.

Being softened in a region defined by the modified surface area may mean that the modified surface area is the deciding factor which determines to which sections inside the plastic part the energy supplied by the heating radiation may be transferred to an extent sufficient to soften the respective region. This makes it possible to control the area in which the plastic part is softened by selective irradiation of the plastic part with the treatment radiation.

In one aspect of the method the plastic part comprises polybutylene terephthalate (PBT).

PBT has particularly good characteristics for the method described above. PBT has a good melting point as well as suitable absorption and reflection properties.

In one aspect of the method the plastic part comprises polytetrafluoroethylene (PTFE).

PTFE may improve the sliding properties of the plastic part. This is particular advantageous if the plastic part is to be incorporated in a drug delivery device and the plastic part is moved during operation of the drug delivery device.

In one aspect of the method the plastic part comprises an additive which changes colour under the influence of the treatment radiation to obtain the modified surface area.

The additive may for example be a dye or a pigment. The additive may for example darken when exposed to radiation of a certain wavelength, e.g. the treatment radiation.

In one aspect of the method the modified surface area of the plastic part has a different colour than the unmodified surface area of the plastic part. The change of the colour may be effected by irradiation with the treatment radiation. The colour change may be one indication for the altered absorption properties of the modified surface area. This means that a defined area of the surface of the plastic part may be changed in its colour by being irradiated with the treatment radiation.

In one aspect of the method the wavelength of the treatment radiation is shorter than the wavelength of the heating radiation. Thus, high energy radiation may be used for treating the surface.

The term "wavelength" as used herein may refer to a main wavelength, like the peak wavelength or the dominant wavelength, of the spectrum of the respective radiation.

In one aspect of the method ultraviolet radiation is used for the treatment radiation.

For example, a wavelength of the treatment radiation is in the range of 300 nm to 400 nm. A wavelength of this range is particularly suitable for treating the reflective surface to obtain a modified surface area.

In one aspect of the method infrared radiation is used for the heating radiation.

For example, a wavelength of the heating radiation is in the range of 900 nm to 1000 nm. A wavelength of this range is particularly suitable for softening the modified surface area.

In one aspect of the method one of the following radiations is or both of the following radiations are coherent electromagnetic radiation: treatment radiation, heating radiation.

In one aspect of the method one of the following radiations is or both of the following radiations are laser radiation: treatment radiation, heating radiation.

In one aspect of the method a laser is used for generating the treatment radiation.

A laser is particularly suitable for generating the treatment radiation because of the wavelength which may be comparatively freely chosen, the high-power of the emitted radiation and/or the small diameter of the laser beam. Because of the small diameter of the laser beam the laser may hit the surface of the plastic part in a small and precisely defined area. Therefore, it is possible that only a small and exact defined part of the surface is converted into the modified surface area. By scanning the surface with the laser beam, a defined pattern of the modified surface area and in particular, an arbitrarily sized modified surface area may be realized even with a laser beam of a small diameter.

In one aspect of the method a laser is used for the heating radiation.

A laser is also particularly suitable for generating the heating radiation. The wavelength and the power of the heating radiation may be adapted to the material which is to be softened, e.g. adapted to the melting point, the glass transition point or the softening point of the material of the plastic part. The use of a laser facilitates that only a precisely defined (sub)section of the modified surface area is irradiated with the heating radiation. Therefore, it is possible that an exactly defined (sub)section of the modified surface area and, consequently, an exactly defined region of the plastic part is softened.

In one aspect of the method the modified surface area forms an inscription on the plastic part.

So it is possible to add an inscription, which may comprise text, one or more numbers, and/or one or more symbols, onto the surface of the plastic part. In particular, preferably the treatment radiation may be used for generating the inscription as well as for defining the softenable region of the plastic part. The heating radiation is expediently applied to a section of the modified surface area being free of the inscription.

The inscription may indicate the type of drug delivery device or the drug contained in and/or to be delivered by the drug delivery device. The inscription may comprise dose-related numbers e.g. for indicating the size of the dose of a drug which is dialed by a user and to be delivered by the drug delivery device.

In one aspect of the method the modified surface area, forms the inscription on the plastic part in a section not irradiated with the heating radiation. So the inscription stays unchanged even after irritation with the heating radiation.

In one aspect of the method, the method additionally comprises the steps: before step B), arranging the plastic part and a further part relative to each other such that a common contact area is formed in which contact area the plastic part mechanically contacts the further part. An extension of the region of the plastic part which is softened in step B) along the contact area may define a joining area in which the plastic part and the further part are to be joined to each other. After step B), the softened region of the plastic part may be cooled and the plastic part and the further part may be joined to each other in the joining area.

The two parts may only be in mechanical contact in the contact area and not yet joined to each other. Only in mechanical contact means the parts may not be permanently connected but can be removed from each other without damaging one of the parts or the permanent connection.

A joint may be formed between the plastic part and the further part. The joint may comprise the permanent connection, e.g. a material connection, like a weld.

The joint in the joining area may result from chemical bonds formed between the plastic part and the further part. The joint may also be realized without chemical bond e.g. by filling undercuts in the surface of the further part with softened material of the plastic part. The plastic part and the further part may be permanently joined to each other.

In one aspect of the method the further part is a further plastic part.

In one aspect, the further part is softenable by the heating radiation. The further part may be softenable without treatment by the treatment radiation or a further treatment radiation. Alternatively, treatment of the further part may be necessary for making the further part softenable by the heating radiation.

In one aspect of the method the further part comprises PBT.

In one aspect of the method the further part comprises PTFE.

It is, for example, possible that the plastic part has been softened by the heating radiation and by cooling the plastic part both parts are joined. But it is also possible that the heating energy is absorbed also by the further part. As a result of this the further part may also be softened. Therefore, the joint may be a result of the cooling of the plastic part and the further part. In this case, it is possible that the softened materials of the first and the further part are mixed with each other. Then, the joint has an extra strength.

In one aspect of the method the modified surface area adjoins the contact area. Preferably the section of the modified surface area which is irradiated in step B) adjoins the contact area. There are embodiments possible in which the modified surface area does not extend over the whole joining area.

In one aspect of the method, in step B), the further part is softened by the heating radiation in a region adjoining the contact area.

In one aspect of the method the modified surface area of the plastic part is arranged on that side of the plastic part which is remote from the further part.

This may be the case, for example, if the plastic part and the further part are arranged on each other. In this case in step A) the surface of the plastic part which is remote from the contact area is preferably irradiated with the treatment radiation. Therefore, the modified surface area is obtained on that side of the plastic part which faces away from the contact area. Thus, the plastic part is also irradiated in step B) with the heating radiation on a surface which is remote from the contact area. In consequence, the joining area may be formed on that side of the plastic part which is remote from the modified surface area.

In one aspect of the method the modified surface area of the plastic part is arranged on a surface of the plastic part which connects the surface of the plastic part which faces the contact area and the surface of the plastic part which faces away from the contact area.

One of the above described methods may be used for manufacturing a drug delivery device. The plastic part may be softened for use in a drug delivery device.

For example it is possible to join a further part for the drug delivery device with the plastic part which may be already located and preferably fixed in a housing for the drug delivery device. Alternatively, the further part may be already located in the housing and the plastic part may be subsequently fixed to the further part. After having treated the surface of the plastic part, it is possible, by irradiating the modified surface area with the heating radiation, to soften the plastic part and/or the further part to form a joining area to permanently connect the plastic part and the further part. Therefore, with this method, it is possible to join, for example, the further part and the plastic part, even if the further part, when arranged in its mounting position with respect to the plastic part, cannot be directly reached by an electromagnetic radiation beam.

Besides the method for manufacturing a drug delivery device, an assembly for a drug delivery device and the drug delivery device itself are also described.

The drug delivery device is particularly used for the administration of medicinal products, particularly of drugs, particularly for self-administration by a patient. The drug delivery devices may be a pen-type injector which dispenses a pre-set dose of the drug. Further, the drug delivery device may be an injection device for single-use or multiple-use.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In one embodiment an assembly for the drug delivery device or the drug delivery device comprises a plastic part and a further part which is firmly joined to the plastic part in a joining area. A surface of the plastic part which faces away from the joining area or adjoins the joining area may have a modified surface area and preferably an unmodified surface area. The plastic part may be softenable in particular in the modified surface area, by irradiating the modified surface area with a pre-given electromagnetic radiation. The plastic part may be unsoftenable in particular in the unmodified surface area, by irradiating the unmodified surface area with said pre-given electromagnetic radiation. The modified surface area may extend along the joining area.

In other words, the drug delivery device or the assembly comprises a plastic part and a further plastic part. The plastic part may be arranged on or beside the further plastic part in a way that the two parts are in mechanical contact with each other and form the contact area. This contact area may comprise the joining area in which the two parts are permanently connected to each other. The first plastic part may comprise the surface with the modified surface area and the unmodified surface area, wherein the modified surface area is expediently capable of absorbing the pre-given electromagnetic radiation to an extent greater than the unmodified surface area. The pre-given electromagnetic radiation may be suitable to soften the plastic part by irradiating the plastic part in the modified surface area. The modified surface area may extend along the joining area.

There are embodiments possible in which the modified surface area covers the whole joining area, or only a part thereof.

In an embodiment the plastic part is arranged beside the further part. The modified surface area preferably adjoins the joining area.

In another embodiment of the drug delivery device or the assembly the plastic part and the further part are joined to each other only in the joining area.

This means that the plastic part and the further part may not be permanently connected to each other over the whole area in which they are in mechanical contact with each other, but only in the joining area. The joining area may comprise, for example, a weld.

The plastic part and the further part may be permanently connected to each other in more than one joining area. Accordingly, the plastic part and the further part may be not connected to each other over the whole area in which they are in contact with each other. Rather, they may be connected, for example, in two separate joining areas. In this case, each of the joining areas may be covered on the side which faces away from the joining area by a surface with a lower reflectivity with respect to the electromagnetic radiation.

In another embodiment of the drug delivery device or of the assembly the drug delivery device is an injection pen.

In another embodiment the plastic part is a dose dial member of the drug delivery device or for the drug delivery device.

Features which are described above and below in connection with the method also apply to the drug delivery device or the assembly and vice versa. Also, features described in connection with different aspects or embodiments may be combined with each other.

Further features, advantages and benefits become apparent from the following description of the exemplary embodiments in conjunction with the accompanying drawings.

BRIEF DESCRIPTION OF THE FIGURES

FIGS. 2a to 2c show a schematic section view of the plastic part and the further part in three different manufacturing steps.

Elements of the same kind and identically acting elements may be designated with the same reference numerals in the figures.

DETAILED DESCRIPTION

Figure 1A:
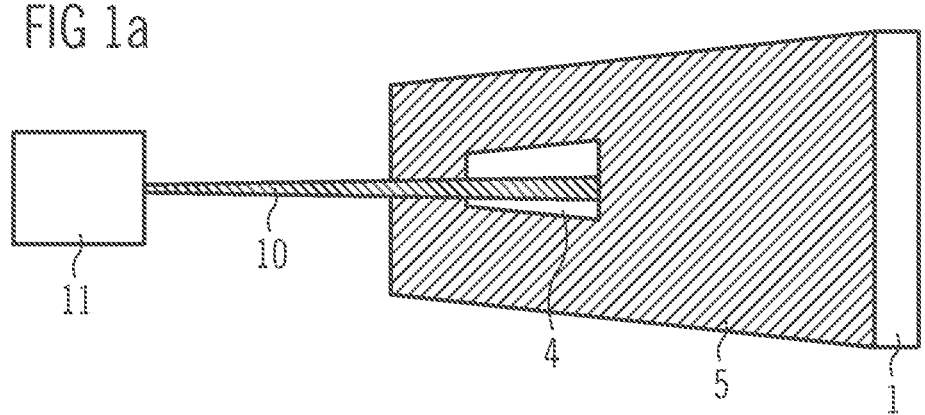
FIGS. 1a to 1c show a schematic section view of the plastic part in three different manufacturing steps.

FIG. 1a shows a plastic part 1 which, for example, may comprise polybutylene terephthalate (PBT) and preferably polytetrafluoroethylene (PTFE), e.g. Celanex 2404MT.

PTFE may improve the sliding properties of the plastic part. The plastic part 1 may additionally comprise an additive like "LaserWhite" 20/9107. The plastic part comprises an unmodified surface area 5 which is reflective for a heating radiation, e.g. laser radiation in the wavelength range of between 900 and 1000 nm such that the plastic part 1 is not softened when irradiated with the heating radiation. In fact, the whole surface may be unmodified before treatment of the plastic part begins.

FIG. 1a shows a treatment radiation source 11 which may emit a treatment radiation 10. The treatment radiation source 11 may, for example, be a laser which emits a laser beam which may have, for example, a peak wavelength in the range of 300 nm to 400 nm, preferably 355 nm, as the treatment radiation 10. An excimer laser may be suitable for the treatment radiation source. By irradiating the unmodified surface area 5 with the treatment radiation 10 the irradiated surface area is altered to be a modified surface area 4. The modified surface area 4 may be modified in its optical characteristics, like having changed its colour, e.g. from white to grey or black, compared to the non-irradiated still unmodified surface area 5 by absorption of the energy of the treatment radiation 10.

Figure 1B:
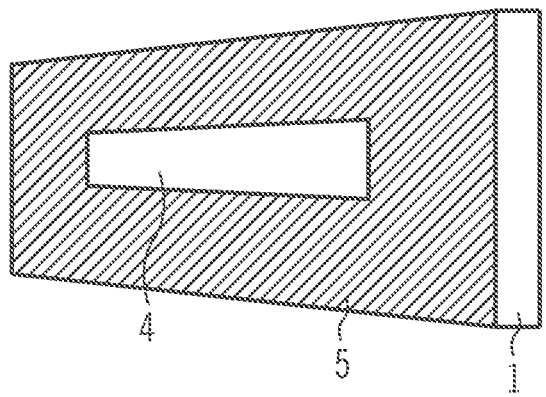

FIG. 1b shows a schematic view of the plastic part 1 which has been treated with the treatment radiation 10. An exact and defined area of the unmodified surface area 5 of the plastic part 1 has now been altered to be a modified surface area 4. The modified surface area 4 expediently absorbs the electromagnetic heating radiation better as compared to the unmodified surface area 5. The electromagnetic heating radiation is particularly suitable for softening the plastic part 1.

There are embodiments possible (not explicitly shown) in which the modified surface area 4 comprises or forms an inscription, which may comprise, for example, text, numbers and/or symbols.

Figure 1C:
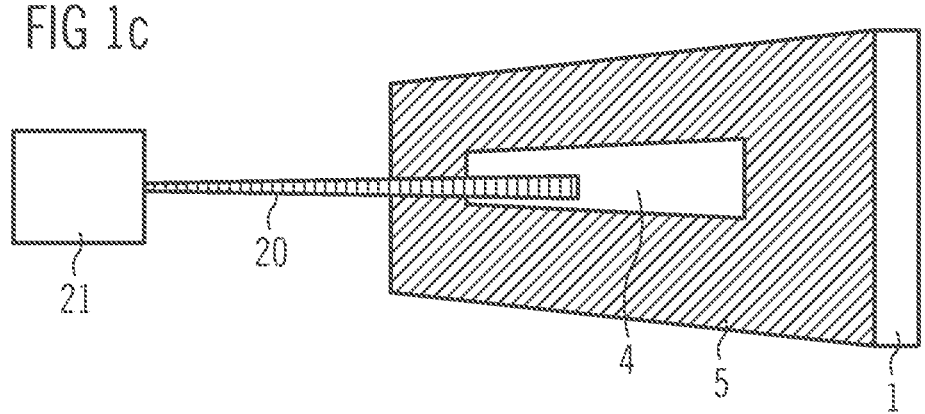

FIG. 1c shows a schematic view of the plastic part 1 in a further manufacturing step. The plastic part 1 which has been pre-treated in a way as shown in FIG. 1a is now irradiated with the heating radiation 20. FIG. 1c shows a heating radiation source 21 that emits the heating radiation 20. For the heating radiation source 21, for example, a laser like a diode laser, may be used. The laser may, for example, emit a heating radiation 20 with a peak wavelength in the range of 900 nm to 1000 nm, preferably 940 nm. As the modified surface area 4 has been pre-treated with the treatment radiation 10 it is now able to absorb the heating radiation 20 better than the untreated unmodified surface area 5. In particular, the plastic part 1 can now be softened by the heating radiation 20 in a region defined by a section of the modified surface area 4 irradiated with the heating radiation 20.

FIG. 2a shows a schematic view of a first manufacturing step of a method for treating a plastic part 1. The FIG. 2a shows a plastic part 1 and a further part 2. The plastic part 1 is arranged on the further part 2. The two parts are in mechanical contact with each other and have a common contact area 6. The plastic part 1 and/or the further part 2 may comprise polybutylene terephthalate (PBT) and preferably polytetrafluoroethylene (PTFE), e.g. Celanex 2404MT. PTFE may improve the sliding properties of the plastic part. The plastic part 1 and/or the further part 2 may additionally comprise an additive like "LaserWhite" 20/9107. The unmodified surface area 5 of the plastic part 1 which faces away from that surface of the plastic part 1 which is in contact with the further part 2 is treated with a treatment radiation 10 similar to the embodiment of FIG. 1. The treatment radiation 10 is emitted by the treatment radiation source 11. The treatment radiation source 11 may, for example, be a laser. The treatment radiation 11 may, for example have a peak wavelength in the range of 300 nm to 400 nm, preferably 355 nm. By treating the unmodified surface area 5 with the treatment radiation 10 the unmodified surface area 5 is altered to the modified surface area 4.

FIG. 2b shows a schematic view of another manufacturing step. The plastic part 1 that has been treated with the treatment radiation 10 before, such as shown in FIG. 2a and described in conjunction therewith, is now able to absorb the energy of a heating radiation 20 to an extent sufficient to soften the plastic part 1. The heating radiation 20 is emitted by a heating radiation source 21. The heating radiation 20 may have, for example, a peak wavelength in the range of 900 nm to 1000 nm, preferably 940 nm. The plastic part 1 is now able to absorb the energy of the heating radiation 20 in the modified surface area 4 and to transfer heating energy to the opposite surface of the plastic part 1 which is contact to the further part 2. Thus, the further part 2 may also be able to absorb a part of the heating energy of the heating radiation 20. The absorbed heating energy may soften the plastic part 1 and/or the further part 2. The plastic part 1 and/or the further part 2 may only be softened in an area which is covered by the modified surface area 4. The unmodified surface area 5 which has not been treated in the previous manufacturing step with the treatment radiation 10 still has a high reflectivity for the heating radiation 20. So, even if the heating radiation 20 hit the plastic part 1 outside of the modified surface area 4, the unmodified surface area 5 would reflect the heating radiation 20 totally or almost totally. In particular, the unmodified surface area 5 would not be softened.

FIG. 2c shows a schematic view of the plastic part 1 and the further part 2 which are now permanently connected with each other in the joining area 3. The joining area 3 is covered by the modified surface area 4 which is located on the surface of the plastic part 1 which faces away from that surface of the plastic part 1 which is in contact with the further part 2. By absorbing the energy of the heating radiation 20 the plastic part 1 and/or the further part 2 has been softened. The softened parts may melt. The melted materials may mix. Additionally or alternatively, the softened plastic part may melt and fill undercuts in the further part (not explicitly shown). A laser weld may be formed as a joint in the joining area. By cooling or curing the softened part(s) for example, the joining area 3 is formed and the plastic part 1 and the further part 2 are joined only in this joining area 3. In the other area, particular an area which is not covered by the modified surface area 4, a joining area 3 cannot be formed and the plastic part 1 and the further part 2 may still be only in contact with each other in the contact area 6 but not permanently connected.

Figure 3A:
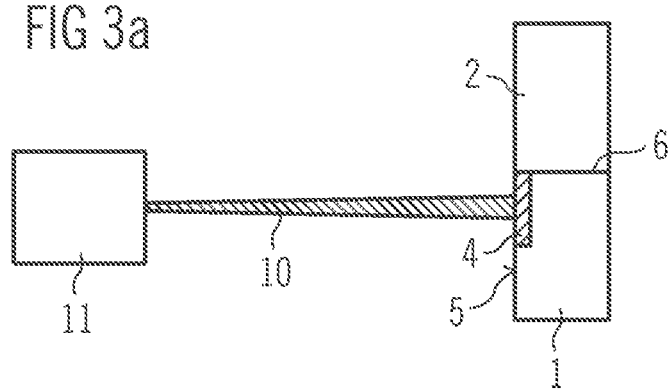
FIGS. 3a to 3c show a schematic section view of the plastic part and the further part in another three different manufacturing steps.

FIG. 3a shows a schematic view of a first manufacturing step of another variant of the manufacturing process. The FIG. 3a shows a plastic part 1 and a further part 2. The plastic part 1 is arranged beside the further part 2, and the two parts are in contact with each other over a side face. A contact area 6 is formed on the side face. The plastic part 1 and/or the further part 2 may comprise polybutylene terephthalate (PBT) and preferably polytetrafluoroethylene (PTFE), e.g. Celanex 2404MT. PTFE may improve the sliding properties of the plastic part. The plastic part 1 and/or the further part 2 may additionally comprise an additive like "LaserWhite" 20/9107. A part of the unmodified surface area 5 of the plastic part 1 which adjoins the further part 2 is treated by a treatment radiation 10 as previously described. The treatment radiation 10 is emitted by a treatment radiation source 11. The treatment radiation source 11 may, for example, be a laser. The treatment radiation 11 may, for example, have a peak wavelength in the range of 300 nm to 400 nm, preferably 355 nm. By treating the unmodified surface area 5 with the treatment radiation 10 the irradiated section of the surface is altered to the modified surface area 4. The modified surface area 4 adjoins the contact area 6.

Figure 3B:
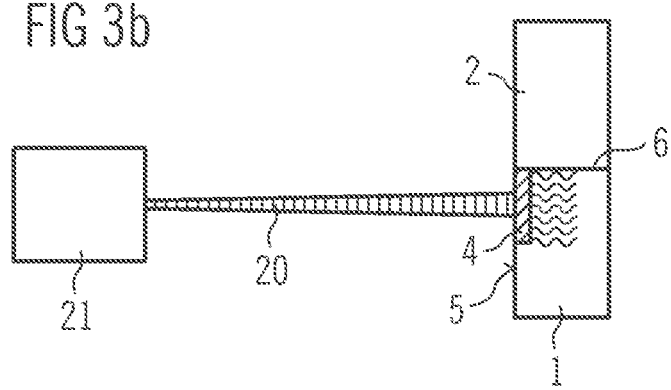

FIG. 3b shows a schematic view of a subsequent manufacturing step. The plastic part 1 that has been treated with the treatment radiation 10 is shown in FIG. 3a. The plastic part 1 is now able to absorb the energy of a heating radiation 20 to an extent sufficient for softening the plastic part 1. The heating radiation 20 is emitted by a heating radiation source 21. The heating radiation source 21 may be, for example, a laser. The heating radiation 20 may have for example a peak wavelength in the range of 900 nm to 1000 nm, preferably 940 nm. The absorbed energy may now soften the plastic part 1 and/or the adjoining further part 2. The plastic part 1 and/or the further part 2 may be softened in an area which is covered by the modified surface area 4 and/or which laterally adjoins this area (not explicitly shown). The unmodified surface area 5 which has not been treated in the previous manufacturing step with the treatment radiation 10 still has a high reflectivity for the heating radiation 20.

Figure 3C:
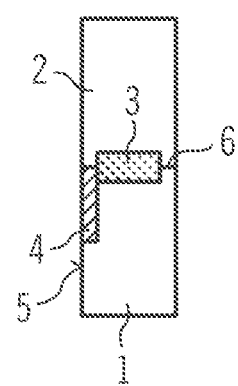

FIG. 3c shows a schematic view of the plastic part 1 and the further part 2 which are now permanently connected with each other in the joining area 3. The joining area 3 is partly covered by the modified surface area 4 and partly adjoins this area. By absorbing the energy of the heating radiation 20 the plastic part 1 and/or the further part 2 has been softened. By cooling or curing the softened part(s) for example, the joining area 3 is formed and the plastic part 1 and the further part 2 are joined only in this joining area 3. In the other area which has not been softened by the absorbed energy the two parts may still be only in mechanical contact with each other, but not permanently connected to each other in a joining area.

Figure 4:
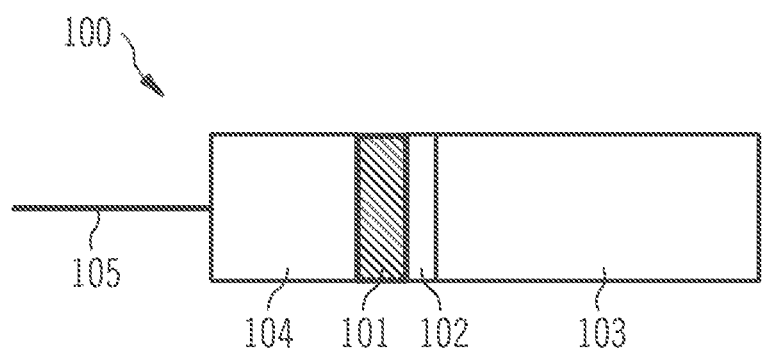
FIG. 4 shows a schematic section view of a drug delivery device comprising the plastic part.

FIG. 4 shows a schematic view of a drug delivery device 100. The drug delivery device 100 comprises a cartridge 102 with a bung 101 moveable retained therein. The other part may be a mount for mounting the dose dial sleeve to the drive unit. The drug delivery device 100 further comprises a drive unit 103. The drive unit 103 may be able to transfer distal force to the bung 101 to drive the bung 101 distally. The drive unit 103 may comprise a plastic part 1 and a further part 2, which are joined to each other in a joining area 3 as described previously. The plastic part 1 or the further part 2 may be a dose dial sleeve. Movement of the bung 101 in the distal direction (to the left in FIG. 4) causes drug 104 which may be retained within the cartridge 102 to be dispensed from the cartridge 102, e.g. through the needle 105. The dose dial sleeve may comprise dose numbers which may be produced by locally treating the unmodified surface area 5 of the dose dial sleeve with the treatment radiation 10. Accordingly the treatment radiation may be used for generating an inscription on the dose dial sleeve as well as for defining a section in which the dose dial sleeve is to be softened.

The invention is not restricted to the exemplary embodiments in the description on the basis of said exemplary embodiments. Rather, the invention encompasses any new feature and also any combination of features which in particular comprises any combination of features in the patent claims and any combination of features in the exemplary embodiments, even if these features or this combination itself is not explicitly specified in the patent claims or exemplary embodiments.

The invention claimed is:

1. Method for treating a plastic part, which comprises a surface, comprising the steps:
    A) irradiating at least a part of the surface with ultraviolet radiation to obtain a modified surface area, the modified surface area being capable of absorbing infrared radiation to an extent greater than the unmodified surface area, and
    B) irradiating the modified surface area with the infrared radiation at least in a section so that the plastic part is heated and softened in a region defined by the irradiated section of the modified surface area.

2. Method according to claim 1, wherein at least a part of the surface of the plastic part which is not irradiated with the treatment radiation is unsoftenable or considerably less softenable by the heating radiation which softens the plastic part in the region defined by the irradiated section of the modified surface area.

3. Method according to claim 1, wherein the modified surface area of the plastic part has a different colour than the unmodified surface area of the plastic part.

4. Method according to claim 1, wherein the plastic part comprises an additive which changes colour under the influence of the treatment radiation to obtain the modified surface area.

5. Method according to claim 1, wherein the modified surface area forms an inscription on the plastic part.

6. Method according to claim 1, additionally comprising the steps:
    before step B), arranging the plastic part and a further part relative to each other such that a common contact area is formed in which contact area the plastic part mechanically contacts the further part, and wherein an extension of the region of the plastic part, which is softened in step B), along the contact area defines a joining area in which the plastic part and the further part should be joined to each other, and,
    after step B), cooling the softened region of the plastic part and joining the plastic part and the further part to each other in the joining area.

7. Method according to claim 6, wherein, in step B), the further part is softened by the heating radiation in a region adjoining the contact area.

8. Method according to claim 6, wherein the modified surface area of the plastic part is arranged on that side of the plastic part which is remote from the further part.

9. Method according to claim 6, wherein the modified surface area of the plastic part is arranged on a surface of the plastic part which connects the surface of the plastic part which faces the contact area and the surface of the plastic part which faces away from the contact area.

10. Method according to claim 6, wherein the modified surface area adjoins the contact area.

11. A method for manufacturing a drug delivery device, comprising
the method of claim 1, wherein the plastic part is softened for use in a drug delivery device.

12. An assembly for a drug delivery device, comprising:
a plastic part,
a further part which is firmly joined to the plastic part in a joining area,
a surface of the plastic part which faces away from the joining area or adjoins the joining area, the surface having a modified surface area created by irradiating with ultraviolet radiation and an unmodified surface area, and the plastic part being softenable by irradiating the modified surface area with infrared radiation and being unsoftenable by irradiating the unmodified surface area with the infrared radiation,
wherein the modified surface area extends along the joining area.

* * * * *